United States Patent

Perry

[11] Patent Number: 6,066,238
[45] Date of Patent: May 23, 2000

[54] HYDROCARBON SEPARATION

[75] Inventor: Graham Michael Perry, Cleveland, United Kingdom

[73] Assignee: Imperial Chemical Industries PLC, London, United Kingdom

[21] Appl. No.: 09/117,661

[22] PCT Filed: Jan. 15, 1997

[86] PCT No.: PCT/GB97/00106

§ 371 Date: Nov. 19, 1998

§ 102(e) Date: Nov. 19, 1998

[87] PCT Pub. No.: WO97/28110

PCT Pub. Date: Aug. 7, 1997

[30] Foreign Application Priority Data

Feb. 3, 1996 [GB] United Kingdom .................... 9602222

[51] Int. Cl.[7] .............................. B01D 3/34; B01D 3/42; C07C 7/05; C07C 7/10
[52] U.S. Cl. ................................. 203/3; 203/43; 203/68; 203/70; 585/802; 585/809; 585/833; 585/836; 585/867
[58] Field of Search ................................ 203/68, 70, 100, 203/3, 71, 43; 585/802, 860, 867, 809, 833, 810, 864, 836; 208/96, 348, 349

[56] References Cited

U.S. PATENT DOCUMENTS

| | | | |
|---|---|---|---|
| 2,348,931 | 5/1944 | Schulze | 203/35 |
| 4,292,141 | 9/1981 | Lindner et al. | 203/70 |

FOREIGN PATENT DOCUMENTS

| | | | |
|---|---|---|---|
| 2158049 | 5/1973 | Germany | 203/70 |
| 2014605 | 8/1979 | United Kingdom . | |

*Primary Examiner*—Virginia Manoharan
*Attorney, Agent, or Firm*—Pillsbury Madison & Sutro Intellectual Property Group LLP

[57] ABSTRACT

A process for the separation of propylene from an input stream of C3 hydrocarbons containing propylene and methyl acetylene and/or propadiene and, optionally, C4 and/or higher hydrocarbons is described. The process includes subjecting the input stream to fractional distillation to separate propylene as an overhead stream leaving a bottoms stream containing the methyl acetylene and/or propadiene and the C4 and/or higher hydrocarbons, when present. A propane-containing stream is added to said input stream whereby propane is separated as part of the bottoms stream. The propylene content of the bottoms streams is maintained at less than 10% weight. The amount of propane added to the input stream is such that the weight of propane, propylene, and C4 and/or higher hydrocarbons, when present, in the bottoms stream is greater that the total weight of methyl acetylene and propadiene in the bottoms stream.

8 Claims, 1 Drawing Sheet

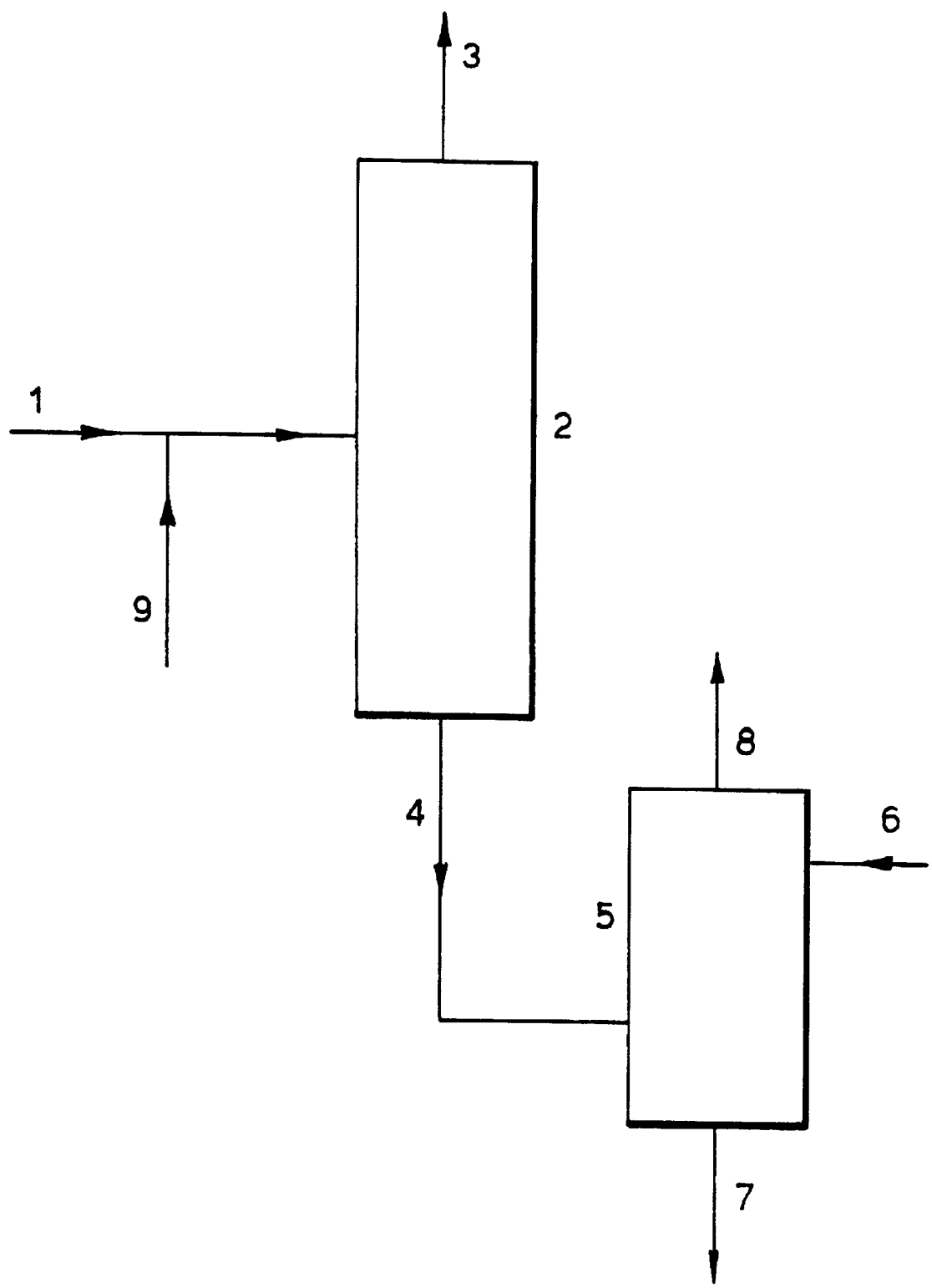

HYDROCARBON SEPARATION

FIELD OF THE INVENTION

This invention relates to hydrocarbon separation and in particular to the separation of hydrocarbons containing three carbon atoms that are more highly unsaturated than propylene, i.e. methyl acetylene and propadiene, from streams consisting of such more highly unsaturated hydrocarbons together with propylene and, optionally, propane. For convenience methyl acetylene and propadiene will collectively be termed MAPD.

BACKGROUND OF THE INVENTION

Hydrocarbon mixtures containing these C3 hydrocarbons may be separated from the product resulting from the steam cracking of hydrocarbon feedstocks such as naphtha. The proportions of the components will depend upon the nature of the feedstock undergoing cracking, the cracking conditions, and any other upstream processing. Typically the C3 stream may contain 0 to 30% by weight propane, 0.1 to 10% by weight MAPD, possibly a small amount, generally less than 1% by weight, of C4 hydrocarbons, and the balance propylene. In some cases, some of the MAPD may be selectively hydrogenated to propylene in an upstream selective hydrogenation reactor. However, it is generally necessary to separate residual MAPD from propylene before the latter is used e.g. for the manufacture of polypropylene.

The separation of MAPD from propylene is conveniently effected by fractional distillation, typically at about 55–60° C. and at a pressure of about 20 bar abs. The propylene is recovered as the overhead stream while the MAPD stream is recovered as the bottoms from the distillation column. Any propane in the feed is recovered with the MAPD as bottoms.

Since MAPD streams are unstable, representing an explosion risk, it is desirable to limit the concentration of MAPD in such a bottoms stream to no more than about 50% by weight: indeed it is often specified that the MAPD concentration should not exceed a somewhat lower level, e.g. 30% by weight.

In order to meet this latter requirement, it is often necessary, especially where the concentration of MAPD in the feed is relatively high and the propane content is less than that of the MAPD, to effect the fractional distillation such that the bottoms stream contains a large proportion of propylene. Since propylene is generally more valuable than propane, this is not economically desirable.

Thus where the MAPD is recovered from the bottoms stream, for example by solvent extraction, e.g. using a polar solvent such as dimethyl formamide, to provide a MAPD stream for subsequent processing, for example for the production of methyl methacrylate, the residual components of the bottoms stream, i.e. propane and/or propylene, could be recycled to the C3 stream being fed to the C3 separation stage producing the aforesaid bottoms stream. However such recycle is often not practical, especially where the recovery of the MAPD from the bottoms stream is effected at a location remote from the site of the C3 separation. As a consequence it is often necessary to use the residual components of the bottoms stream, after separation of the MAPD therefrom, as fuel. This is not an economic use of the more valuable propylene in that bottoms stream.

Where it is not desired to recover the MAPD from the bottoms stream, the bottoms stream can be recycled to the cracker as part of the feedstock thereto. However where the bottoms stream contains a large proportion of propylene, this represents a waste of the valuable propylene.

SUMMARY OF THE INVENTION

In the present invention, this problem is overcome by adding propane to the feed to the C3 separation stage so that it is not necessary to operate the C3 separation such that the bottoms stream contains a large proportion of propylene: it becomes possible to operate the C3 separation such that the bottoms stream contains less than 10%, particularly less than 5%, by weight of propylene. As a result the amount of propylene in the C3 feed that can be recovered as overheads is increased.

Accordingly the present invention provides a process for the separation of propylene from a input stream of C3 hydrocarbons containing propylene and methyl acetylene and/or propadiene and possibly also C4 and/or higher hydrocarbons, comprising subjecting said input stream to fractional distillation to separate propylene as an overhead stream leaving a bottoms stream containing said methyl acetylene and/or propadiene and said C4 and/or higher hydrocarbons (if any), characterised in that a propane-containing stream is added to said input stream whereby propane is separated as part of said bottoms stream, and so that the propylene content of the bottoms stream can be maintained at less than 10%, preferably less than 5%, by weight, the amount of propane added to said input stream is such that the weight of propane, propylene, and C4 and/or higher hydrocarbons (if any) in said bottoms stream is greater than the total weight of methyl acetylene and propadiene in said bottoms stream.

The propane-containing stream that is added may be any propane-containing stream that is conveniently or economically available for the present purpose. It may be essentially pure propane or, more usually, will be a stream containing propane in admixture with other C3 and/or higher hydrocarbons, but preferably contains little or no MAPD. Preferably the propane-containing stream contains at least 15% by weight of propane. Examples of such gas streams include propane fractions containing at least 90%, particularly at least 95%, by weight of propane, and "refinery propylene" which typically contains 20–35% by weight of propane, balance essentially propylene.

It will be seen that, averaged over a period of time, the amounts of propane, any C4 and/or higher hydrocarbons, and the amount of MAPD, in the feed to the fractional distillation equal the amounts of propane, any C4 and/or higher hydrocarbons, and MAPD removed from the fractional distillation as said bottoms stream. Consequently, if it is desired that the MAPD content of the bottoms stream is kept below X% by weight, and the propylene content below Y%, then the amount of propane plus any C4 and/or higher hydrocarbons in the feed to the fractional distillation should be such that the weight ratio of propane plus any C4 and/or higher hydrocarbons to MAPD of the fractional distillation feed is greater than (100−X−Y)/X.

BRIEF DESCRIPTION OF THE DRAWING

The invention is illustrated by reference to the accompanying drawing which is a diagrammatic flow sheet.

DETAILED DESCRIPTION OF THE PREFERRED EMBODIMENTS

Referring to the drawing, a C3 hydrocarbons stream 1 containing propylene and MAPD, for example as resulting from a cracker after separation of the C2 hydrocarbons and low boiling point components (such as methane, hydrogen, carbon monoxide) and higher boiling components such as C4 and higher hydrocarbons, is fed to a fractional distillation column 2 where it is split into an overheads stream 3 consisting essentially of propylene and a bottoms stream 4 containing the MAPD. The stream 1 may contain a small proportion, usually less than 1% by weight, of C4 and/or higher hydrocarbons. Such C4 and/or higher hydrocarbons will be separated as part of the bottoms stream. The bottoms stream may be recycled directly to the cracker or, as shown in the drawing, passed to a solvent extraction vessel 5 (possibly after a further separation stage where any higher boiling point components, e.g. C4 and/or higher hydrocarbons, are removed). In extraction vessel 5 the MAPD is extracted with a solvent such as dimethyl formamide fed via line 6. The MAPD solution leaves the extraction vessel via line 7 and may be further processed, for example used to make methyl methacrylate. The overheads 8 from the extraction vessel may be used as fuel or otherwise employed.

In order to maintain the concentration of MAPD in the bottoms stream 4 at a safe level, propane is added to the teed 1 via line 9. Provided sufficient propane is present in the mixture of the original feed 1 and the propane added via line 9 that the weight ratio of propane plus any C4 and/or higher hydrocarbons to MAPD in this mixture is equal to or above the aforesaid safe level, the fractional distillation column 2 may be operated such that little or no propylene is slipped as part of the bottoms stream 4.

The stream of additional propane added via line 9 may, if practical in the circumstances, be in part formed from the overheads stream 8 augmented as necessary with fresh propane from an external source. Alternatively, where practical, the overheads stream 8 may be returned as part of the feed to the cracker producing the feed stream 1, or to another cracker.

Where it is not desired to recover the MAPD stream from the bottoms stream 4, a catalytic selective hydrogenation unit may be provided upstream of the fractional distillation column 2, and preferably before the addition of the propane stream 9, to convert some of the MAPD to propylene. In this case, the amount of propane that need be added via line 9 may be small, and the bottoms stream 4 can be recycled to the cracker producing the feed to the selective hydrogenation unit, or to another cracker. It will be appreciated that even where there is such a selective hydrogenation unit, addition of propane may be desirable as aforesaid to enable the selective hydrogenation unit to be taken off-line for e.g. maintenance and/or catalyst replenishment.

The invention is illustrated by the following example in which all parts and percentages are by weight.

A C3 stream having the composition (90.8% propylene, 4.5% propane, 2.7% methyl acetylene, 1.8% propadiene, 0.2% C4 and higher hydrocarbons) separated from the product of steam cracking of naphtha was fed at a rate of 48 te/h and at a pressure of 17 bar abs and a temperature of 45° C. to a distillation column. In order to obtain a bottoms stream containing less than 25% MAPD, it was necessary to operate the distillation column such that the overhead stream consisted of 39.4 te/h of 99.6% propylene, 0.4% propane and less than 2 ppm of MAPD and the bottoms stream consisted of 8.6 te/h of a mixture having the composition 25% MAPD, 23% propane, 1% C4 and higher hydrocarbons and 51% propylene. It is seen that a substantial amount, 4.4 te/h, of propylene was contained in the bottoms stream.

In accordance with the invention, a propane-containing stream having the composition 95% propane and 5% butane was added at a rate of 4.2 te/h to the C3 stream before feeding to the distillation column. As a result the distillation column could be operated, again giving a bottoms stream containing the same % MAPD, to give an overhead stream consisting of 43.5 te/h of the same composition as previously, i.e. 99.6% propylene, 0.4% propane and less than 2 ppm of MAPD, and a bottoms stream consisting of 8.6 te/h of 25% MAPD, 69% propane, 4% C4 and higher hydrocarbons, and 2% propylene.

It is seen that the amount of propylene separated as the overheads stream increased by 11% and the bottoms stream contained little propylene.

The MAPD could be separated from the bottoms stream by solvent extraction and the unextracted gas from the bottoms stream could be used as fuel. Alternatively the unextracted gas from the bottoms stream could be recycled to the cracker or, after taking a small purge to avoid build up of C4 and higher hydrocarbons, recycled to the C3 stream.

What is claimed is:

1. A process for the separation of propylene from a input stream of C3 hydrocarbons containing propylene and methyl acetylene and/or propadiene and, optionally, C4 and/or higher hydrocarbons, comprising subjecting said input stream to fractional distillation to separate propylene as an overhead stream leaving a bottoms stream containing said methyl acetylene and/or propadiene and said C4 and/or higher hydrocarbons, when present, wherein a propane-containing stream is added to said input stream whereby propane is separated as part of said bottoms stream, and the propylene content of the bottoms stream is maintained at less than 10% weight, the amount of propane added to said input stream being such that the weight of propane, propylene, and C4 and/or higher hydrocarbons, when present, in said bottoms stream is greater that the total weight of methyl acetylene and propadiene in said bottoms stream.

2. A process according to claim 1 wherein the amount of propane plus any C4 and/or higher hydrocarbons in a feed to the fractional distillation is such that the weight ratio of propane plus any C4 and/or higher hydrocarbons to methyl acetylene and/or propadiene in the fractional distillation feed is greater than $(100-X-Y)/X$, the methyl acetylene and/or propadiene content of the bottoms stream being kept below X% by weight and the propylene content of the bottoms stream being kept below Y% by weight.

3. A process according to claim 1 wherein methyl acetylene and/or propadiene is recovered from the bottoms stream by solvent extraction.

4. A process according to claim 1 wherein the input stream is a stream of C3 hydrocarbon components separated from the product of steam cracking a hydrocarbon feedstock.

5. A process for the separation of propylene from a input stream of C3 hydrocarbons containing propylene and methyl acetylene and/or propadiene and C4 hydrocarbons, comprising subjecting said input stream to fractional distillation to separate propylene as an overhead stream leaving a bottoms stream containing said methyl acetylene and/or propadiene and said C4 hydrocarbons, wherein a propane-containing stream is added to said input stream whereby propane is separated as part of said bottoms stream, and so that the propylene content of the bottoms stream is maintained at less than 10% weight, the amount of propane added to said input stream being such that the weight of propane, propylene, and C4 hydrocarbons in said bottoms stream is greater that the total weight of methyl acetylene and propadiene in said bottoms stream.

6. A process according to claim 5 wherein the amount of propane plus any hydrocarbons in a feed to the fractional distillation is such that the weight ratio of propane plus any C4 hydrocarbons to methyl acetylene and/or propadiene in the fractional distillation feed is greater than $(100-X-Y)/X$ such that the methyl acetylene and/or propadiene content of the bottoms stream is kept below X% by weight and the propylene content of the bottoms stream is kept below Y% by weight.

7. A process according to claim 5 wherein methyl acetylene and/or propadiene is recovered from the bottoms stream by solvent extraction.

8. A process according to claim 5 wherein the input stream is a stream of C3 hydrocarbon feedstock.

* * * * *